US012648817B2

(12) United States Patent
Sutula et al.

(10) Patent No.: US 12,648,817 B2
(45) Date of Patent: Jun. 9, 2026

(54) BIOMECHANICAL MODEL FOR PREDICTING DEFORMATIONS OF A PATIENT BODY

(71) Applicant: Brainlab SE, Munich (DE)

(72) Inventors: Danas Sutula, Munich (DE); Max Langhof, Munich (DE)

(73) Assignee: BRAINLAB SE, Munich (DE)

( * ) Notice: Subject to any disclaimer, the term of this patent is extended or adjusted under 35 U.S.C. 154(b) by 215 days.

(21) Appl. No.: 18/559,312

(22) PCT Filed: Mar. 20, 2023

(86) PCT No.: PCT/EP2023/057080
§ 371 (c)(1),
(2) Date: Nov. 6, 2023

(87) PCT Pub. No.: WO2023/175192
PCT Pub. Date: Sep. 21, 2023

(65) Prior Publication Data
US 2024/0225738 A1 Jul. 11, 2024

(30) Foreign Application Priority Data

Mar. 18, 2022 (WO) ................ PCT/EP2022/057222

(51) Int. Cl.
*A61B 34/10* (2016.01)
*G06T 7/00* (2017.01)

(52) U.S. Cl.
CPC ............ *A61B 34/10* (2016.02); *G06T 7/0012* (2013.01); *A61B 2034/104* (2016.02); *A61B 2034/105* (2016.02); *G06T 2207/30004* (2013.01)

(58) Field of Classification Search
None
See application file for complete search history.

(56) References Cited

U.S. PATENT DOCUMENTS 11,877,809 B2 * 1/2024 Vilsmeier .............. A61B 34/10
2016/0247312 A1 * 8/2016 Santhanam ............... G06T 7/33
(Continued)

FOREIGN PATENT DOCUMENTS

WO 2021122456 A1 6/2021
WO 2023175192 A1 9/2023

OTHER PUBLICATIONS

Brainlab, Intraoperative Plan Update, Elements Virtual IMRI Cranial, 11 pages, dated Jun. 25, 2020.
(Continued)

*Primary Examiner* — Nancy Bitar
(74) *Attorney, Agent, or Firm* — Gray Ice Higdon

(57) ABSTRACT

The present invention relates to computer-implemented method of predicting a deformation of at least one part of a patient body, a corresponding computer program, a program storage medium with such a program, as well as a medical system. The method comprises the steps of providing a computer simulatable biomechanical model of the at least one part of a patient body (step S1); carrying out S>1 forward simulations of the biomechanical model thereby calculating S resulting deformation vectors (step S2); calculating an approximated biomechanical model based on the S resulting deformation vectors (step S3); acquiring pre-operative data (step S4); optimizing, in a calculative manner, a deformation predicted by the approximated biomechanical model, which results in an optimized, predicted deformation vector (step S5); and deforming the pre-operative data by applying the optimized, predicted deformation vector to the pre-operative patient data (step S6). Particular embodiments of said calculation of the approximated biomechanical model entail different embodiments of a multivariate interpolation, and/or entail different embodiments of a mode decomposition.

30 Claims, 5 Drawing Sheets

(56) References Cited

U.S. PATENT DOCUMENTS

| | | |
|---|---|---|
| 2017/0148213 A1 | 5/2017 | Thomas |
| 2020/0179051 A1* | 6/2020 | Miga ..................... G16H 80/00 |

OTHER PUBLICATIONS

Heiselman et al., Journal of Medical, Imaging Characterization and correction of intraoperative soft tissue deformation in image-guided laparoscopic liver surgery, dated 2017.
Sun et al., IEEE Journal of Translational Engineering in Health and Medicine, Near Real-Time Computer Assisted Surgery for Brain Shift Correction Using Biomechanical Models, dated 2014.
Miga et al., Neurosurgery, Modeling of Retraction and Resection for Intraoperative Updating of Images, dated 2021.
Peterlik et al., Computers & Graphics, Real-time visio-haptic interaction with static soft tissue models having geometric and material nonlinearity, dated 2009.
International Searching Authority, International Search Report and Written Opinion issued in Application No. PCT/EP2023/057080, 17 pages, dated May 2, 2023.
Hou Wengo et al., A New Deformation Model of Brain Tissues for Neurosurgical Simulation, IEEE, vol. 69, No. 4, 8 pages, dated Apr. 1, 2020.
European Patent Office, Examination Report issued in Application No. 23710790.9, 5 pages, dated Mar. 4, 2026.

\* cited by examiner $$f(0) = A = \boxed{0}\, u_1 + \boxed{0}\, u_2$$
$$f(0,5) = B = \boxed{2}\, u_1 + \boxed{0}\, u_2$$
$$f(1) = C = \boxed{3}\, u_1 + \boxed{1}\, u_2$$

$$W_1(p) \qquad W_2(p)$$

$$\Rightarrow$$

$$W_1(0) = 0$$
$$W_1(0,5) = 2$$
$$W_1(1) = 3$$
$$W_2(0) = 0$$
$$W_2(0,5) = 0$$
$$W_2(1) = 1$$

mode space:

$$W(p) = \begin{pmatrix} W_1(p) \\ W_2(p) \end{pmatrix}$$

BIOMECHANICAL MODEL FOR PREDICTING DEFORMATIONS OF A PATIENT BODY

FIELD OF THE INVENTION

The present invention relates to computer-implemented method of predicting a deformation of at least one part of a patient body, a corresponding computer program, a program storage medium with such a program, as well as a medical system.

TECHNICAL BACKGROUND

The presented invention concerns the problem of predicting, in a calculative, computer implemented manner, the deformation that organs and tissues within a patient undergo during a surgical intervention. The goal of such a prediction is to apply this deformation to pre-operative data so as to align it with the state currently observed in the patient. Several prior art solutions are exiting already, however, all these techniques known in the prior art do have particular drawbacks, as will be explained in more detail.

In neurosurgery, the prediction of intra-operative deformations primarily relates to "brain shift", i.e., the deformation of the patient brain during and due to the surgical intervention. Brainlab presently markets and sells the product "Virtual iMRI Cranial" for correction of brain shift. This system defines the Gold Standard for applications after a tumour resection. The method used therein constructs a parametrized, patient-specific biomechanical model of the cranial anatomy. It subsequently employs an optimization algorithm to solve the inverse problem of finding model parameters that best match a given intra-operative datum to the model-predicted deformation of pre-operative data. However, the approach employed in the current Brainlab Virtual iMRI Cranial product has the drawback of requiring multiple minutes of computation after arrival of intra-operative data to obtain a brain shift correction, as a parametrized model is built and explored by a derivative-free optimization algorithm in an online fashion. This may cause a significant disruption to the surgical workflow, which the presented method can eliminate.

A similar approach is used by Sun et al in their study *"Near Real-Time Computer Assisted Surgery for Brain Shift Correction Using Biomechanical Models"* published IEEE Journal of Translational Engineering in Health and Medicine, Volume 2, 2014, where a parametrized patient-specific biomechanical model is employed for brain shift prediction, too. This method samples the parameter space uniformly to obtain a set of deformations prior to acquisition of intra-operative landmark data. A least-squares fit is then used to obtain an optimal linear combination of these deformations with respect to the landmark data. However, this approach fundamentally requires that a set of point displacements be known (e.g., through detection of landmark pairs) in order to compute the least squares fit. This means that it cannot be used with other forms of intraoperative data (e.g., 3D intraoperative imaging). Further, since the landmark data as described in this publication can only be acquired on the surface of the brain, it is infeasible to ascertain the deformation of brain structures below the surface (e.g., ventricles) with this approach.

Moreover, in 2017 Heiselman et al. published in their paper *"Characterization and correction of intraoperative soft tissue deformation in image-guided laparoscopic liver surgery"*, Journal of Medical Imaging, April-June 2018, Vol.

5 (2), the consideration of the problem of tissue deformation in laparoscopic liver surgery. Using a fully linear biomechanical model, a set of deformation modes based on control point deformations is established. A linear combination of these modes is subsequently optimized to fit the intra-operative data. This approach relies strongly on the linearity of the employed simulation model, whereas the presented method can also be used with more advanced biomechanical models that allow for non-linear effects. This restriction also precludes use of this method for tackling more complex intraoperative scenarios, such as those considered in the parametrized biomechanical models mentioned before.

Therefore, the inventors of the present invention had identified the need of providing an improved prediction of deformations of a patient's body that overcomes at least some of the drawbacks of the known techniques.

EXEMPLARY SHORT DESCRIPTION OF THE INVENTION

In the following, a short description of the specific features of the present invention is given which shall not be understood to limit the invention only to the features or a combination of the features described in this section.

The disclosed method provides a computer-implemented method of predicting a deformation of at least one part of a patient body. In detail, a computer simulatable biomechanical model of the at least one part of a patient body is provided. The model may be pre-calculated, and the presented method may just acquire the pre-calculated model from e.g., a server, on which the model is stored, or from any other kind of data storage device. However, as will be explained in more detail hereinafter, in particular embodiments of the present invention the presented method comprises the generation of the computer simulatable biomechanical model, i. e., the process of building the computer simulatable biomechanical model. This step of generating the biomechanical model may then use pre-operative data. This will be explained in detail hereinafter in the context of particular embodiments.

In general, the biomechanical model is a parametrized, patient-specific biomechanical model for predicting the deformation of the at least one part of the patient body. In one exemplary embodiment, the biomechanical model is a simulation model of the relevant organs and tissues of the patient, for example the brain tissue, in case of a cranial intervention.

For said deformation prediction the computer implemented method carries out S>1 forward simulations of the biomechanical model, by means of which S resulting deformation vectors are calculated. These S resulting deformation vectors are then used to calculate the approximated biomechanical model. Moreover, an optimization of the deformation, which is predicted by the approximated biomechanical model, is carried out, which results in an optimized, predicted deformation vector. As is apparent for the skilled reader from the present disclosure, this optimization is a computer implemented calculation. The optimized, predicted deformation vector, which is calculated in this way, is then used to deform pre-operative data by applying the optimized, predicted deformation vector to the pre-operative patient data.

In other words, the purpose of the simulation model is to predict deformations of the pre-operative patient state ("forward solution"). That is, the result computed by running such a ("forward") simulation is a physically plausible deformation of the patient anatomy from the pre-operative state to some intra-operative state presented by some intra-operative data about the patient. In the end, the practitioner/user would like the computed deformation to closely match the pre-operative data to some observed intra-operative state of the patient. The presented method matches this need and provides a fast and accurate method of calculate a deformation, which needs to be applied to the pre-operative data in order to best match or to be ideally fully aligned with the intra-operative data.

As was explained before, in the presented method, the simulation model is "explored" in an initial phase by performing several forward simulations, followed by preparing an approximation of the model. Crucially, this phase may happen before intra-operative data is acquired, and can thus be done before an alignment between pre-operative and intra-operative data is calculated by the computer or medical system carrying out the presented method or by any user. This in turn allows a suitably chosen optimization procedure to rapidly compute the desired deformation. The pre-operative data can thus be deformed to match the current patient state, i.e. the intra-operative data, with minimal time expenditure after acquisition of intra-operative data. This deformation can of course also be used as a starting point for computation of further updates, should new intra-operative data become available. Thus, the presented method provides an accurate and fast way of predicting the deformation that, for example, organs and tissues within a patient undergo during a surgical intervention. The presented method allows for applying this deformation to, e.g. high-fidelity, annotated and/or enriched pre-operative data so as to align it with the state currently observed in the patient. The prediction, i.e., the method defined herein by steps S1 to S6, can be informed by the acquisition of possibly sparse, partial, and/or low-fidelity intra-operative data.

As will become apparent from the details explained herein, the present invention provides a means of establishing an accurate prediction requiring minimal time after the intra-operative data acquisition.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented method of predicting a deformation of at least one part of a patient body. The method comprises the steps of providing a computer simulatable biomechanical model of the at least one part of a patient body (step S1);

wherein the biomechanical model is a parametrized, patient-specific biomechanical model for predicting the deformation of the at least one part of the patient body, the method further comprising the steps carrying out S>1 forward simulations of the biomechanical model thereby calculating S resulting deformation vectors (step S2);

calculating an approximated biomechanical model based on the S resulting deformation vectors (step S3);

acquiring pre-operative data (step S4);

optimizing, in a calculative manner, a deformation predicted by the approximated biomechanical model, which results in an optimized, predicted deformation vector (step S5); and deforming the pre-operative data by applying the optimized, predicted deformation vector to the pre-operative patient data (step S6).

According to the first aspect, the presented method comprises the use of an approximated biomechanical model that is calculated and that this approximation is used for the optimization of the deformation/deformation field, which is in contrast to and distinct over prior art techniques, as will be explained in more detail hereinafter. Particular embodiments of said calculation of the approximated biomechanical model entail different embodiments of a multivariate interpolation, and/or entail different embodiments of a mode decomposition. This will be explained in more detail hereinafter in the context of particular embodiments.

The inventors of the present invention have found that in this way the deformed pre-operative data can be provided in a comparatively short amount of time, while a high accuracy of the prediction of the deformation can still be ensured. In one embodiment, these deformed pre-operative data can then be displayed to the user, as will be elucidated hereinafter in more detail.

The presented method can beneficially make use of the time before a surgical intervention takes place and can carry out step S1, S2 and S3 before such an intervention. Thus, the provision of the computer simulatable biomechanical model (step S1), the S>1 forward simulations of the biomechanical model together with the calculation of the S resulting deformation vectors (step S2), as well as the calculation of the approximated biomechanical model based on the S resulting deformation vectors (step S3) can beneficially be carried out before such an intervention which can save valuable calculation time when running calculations during an intervention. In that sense, the presented method allows for a highly efficient pre-calculation of the approximated biomechanical model.

Note that the step S2 described herein (i.e., carrying out S>1 forward simulations of the biomechanical model thereby calculating S resulting deformation vectors) does not have to be carried out iteratively. Thus, the S simulations do not have to be carried out in an iterative manner. The simulations can be carried out one after another or can be out fully or partly in parallel. As is clear to the skilled reader this may be understood as a sampling of the parameter space. This will be explained in more detail in the context of the particular, non-limiting example of FIG. 7.

Furthermore, regarding step S2, in an embodiment the S simulations differ in their input parameter value combinations. As was explained before, the biomechanical model is a "parametrized" biomechanical model. This will be explained in more detail in the context of the particular, non-limiting example of FIG. 7. As is clear to the skilled reader, using the same input parameter value combinations does not provide new information.

Moreover, the presented method not only calculates a single deformation vector. It calculates S deformation vectors and hence more than one deformation vector. The presented method performs S different simulations, each resulting in a deformation vector. As was explained before, the presented method explicitly builds an approximation of the underlying biomechanical model by using the S deformation vectors of said S simulations. Thus, the presented method relates to building and using an approximation of a biomechanical model based on several simulations that were performed ahead of time.

Positively, the presented method places no restriction on the underlying model. It can be used with state-of-the-art finite element techniques that can accurately model complex deformations, which are usually what one is interested in when applying biomechanical modeling techniques in the first place.

As will become apparent from the present disclosure, the "deformation" or "deformations" of the present invention are physical deformations of a patient's body or of parts thereof. In other words, such "deformations" are to be understood as deformations that patient bodies and/or patient tissues generally undergo. This will be explained in more detail hereinafter.

During surgery, patient bodies/patient tissues generally undergo deformations, which may lead to a mismatch between pre-operative planning data and reality. The purpose of the presented computer implemented method is to facilitate a correction of such deformations, which is achieved by calculating said optimized, predicted deformation vector by means of said steps S1 to S5 detailed hereinbefore and hereinafter. As is clear to the skilled reader, when deforming the pre-operative data in step S5 by applying said optimized, predicted deformation vector to the pre-operative patient data, said correction is realized.

Moreover, as is apparent from the present disclosure, in some embodiments the step S5 of optimizing the deformation predicted by the approximated biomechanical model may comprise several iterations until the optimized, predicted deformation vector is determined. As is typical in optimization procedures, an iterative process may be used to get, iteration by iteration, closer to the finally determined optimized, predicted deformation vector. Also this will be explained in more detail hereinafter, for example in the context of the embodiment of FIG. 6.

As part of the normal surgical procedure, pre-operative data, like e.g., planning data is acquired before surgery. This data typically depicts the pre-operative patient anatomy, usually in high quality and with intervention-specific annotations (e.g., outlined tumour and/or edema, fiber tracts, landmarks). Further data may be acquired specifically to inform an optionally comprised simulation model construction/generation. For example, information about the surgical plan, e.g., the intended approach to the surgical site, may be incorporated, or the intraoperative gravity direction with respect to the patient brain measured. During the optimization of the calculated predicted deformation, an observation of the current patient state during the intervention can be used. Thus, intra-operative data can be acquired in particular embodiments, for example by CT, MRI or US imaging, or by acquisition of point or surface data, as will be explained hereinafter in detail. This data may be sparse, e.g., few slices/points, partial, e.g., the field of view covers only part of the surgical site, or of low or lower fidelity, e.g., low resolution, low accuracy, as compared to typical pre-operative data. The reduced quality of this intra-operative data is generally due to a trade-off between acquisition quality and acquisition speed, as time is an important constraint during surgical interventions.

Preferably, in the optimization step S5 mentioned hereinbefore, an algorithm is used to determine a reasonable, preferably non-rigid, deformation that aligns the pre-operative data and the intra-operative data. Since the pre-operative data is no longer in line with reality, whereas intra-operative data represents an observation of the current patient state, one can deform the pre-operative data with the computed deformation, i.e., with the optimized, predicted deformation vector determined in step S5, so that it matches the intra-operative data, and thus, presumably, the current patient state. In effect, this computer-implemented method embodiment provides the desired alignment of the preferably high quality pre-operative data to the current patient state, using preferably only quick-to-acquire, low quality intra-operative data during the surgical intervention. Thus, in a particular embodiment, the presented method can comprise the step of acquiring pre-operative data for such an alignment, as will be explained in more detail hereinafter in the context of particular embodiments.

As is apparent from the present disclosure, the purpose of the approximation of the model is speeding up the optimization procedure, but not by having fewer degrees of freedom than the original model. Rather, the approximation (once established) is much simpler and faster to compute. And in a particular embodiment the approximation is differentiable, which will be explained in detail later on, both of which substantially benefit the speed of the optimization procedure.

Regarding the computer simulatable biomechanical model, i.e., the simulation model, and regarding the forward simulations the following should be noted. The presented method does not entail the need to make any assumptions about the mathematical, biological or physical underpinnings of the simulation model, or the means by which a solution is computed, which differs from the state of the art. Only two conceptual properties of the simulation model should, preferably, be taken into account: First, the computed deformations should preferably be representable as vectors of N real numbers, and second the simulation model can be parametrized by $P \geq 1$ scalar parameters. Representing a deformation as a vector of N real numbers is standard practice, for example by numbering the nodes of a grid from 1 to K and storing each of the $N = 3$ K translational nodal degrees of freedom. The assumption of a parametrized model stems from the fact that not every phenomenon during surgical intervention can be predicted a-priori. For example, the following properties could be influenced by/during the course of surgery: The amount of mass effect reversal due to tumour resection, in cranial cases, the amount of cerebrospinal fluid drained from the skull, the amount of pressure applied by a surgical tool (e.g., an ultrasound probe), changes in tissue properties (e.g., stiffness, compressibility) due to e.g., medication. The computer simulatable biomechanical model can incorporate these effects and control their "strength" with corresponding parameters. Thus, deformations can be predicted for different surgical scenarios by performing simulations with different choices for the parameter values.

One approach to remedying e.g., observed brain shift using such a simulation model is therefore to search values for the parameters that best align the observed pre- and intra-operative states of the patient—an inverse problem. For this, for example a cost function can be established for comparing deformed pre-operative data with newly acquired intra-operative data. This cost function, for example image similarity or landmark distances, or the like, can then be optimized by a derivative-free optimization algorithm: For a given choice of parameter values, perform a simulation to obtain a corresponding deformation, evaluate the cost function for this deformation, and report the cost value to the optimization algorithm. The optimization algorithm then either proceeds to select a new set of parameter values, or, after several iterations, asserts convergence.

A major drawback in some prior art approaches is the fact that the cost function can only be computed once intra-operative data has already been acquired. Therefore, in prior art approaches the space of possible deformations ("deformation space") must be explored "online", i.e. while a user is currently waiting for a result. This disadvantage is overcome by the method as presented herein.

Regarding the preparation of the approximation of the computer simulatable biomechanical model, one valuable aspect of the method described here is the idea of exploring the deformation space "offline". This involves carrying out S forward simulations prior to acquisition of intra-operative data and condensing the S simulation results into a form that enables fast optimization, e.g., a fast optimization of a cost function. As will be explained in detail hereinafter, specifically, two groups of techniques for "condensing" the obtained solution data are considered. First, a direct multivariate interpolation of the S simulation results, and second a decomposition of the set of predicted deformations into multiple independent "deformation modes". This will be elucidated in the context of particular embodiments.

Note that in an embodiment, the method comprises executing, on at least one processor of at least one computer, the method steps mentioned hereinbefore, which are executed by the at least one processor. This holds not only true for this first aspect of the present invention, but also for all the other computer implemented method embodiments disclosed hereinafter.

According to an embodiment of the presented method, the method comprises acquiring intra-operative data. Moreover, in the step S5 of carrying out the optimization, with which the optimized, predicted deformation vector is determined, the alignment between the acquired pre-operative, which are deformed with the determined deformation vector, and with the acquired intra-operative data, is optimized.

That is, the result computed by running such a forward simulation is a physically plausible deformation of the patient anatomy from the pre-operative state to some intra-operative state presented by some intra-operative data about the patient. In the end, the practitioner/user may like the computed deformation to closely match the pre-operative data to some observed intra-operative state of the patient. The presented embodiment matches this need and provides a fast and accurate method of calculating a deformation, which needs to be applied to the pre-operative data, in order to best match or to be ideally fully aligned with the intra-operative data. This aspect can also be gathered from the detailed, non-limiting embodiments of FIGS. 3 and 7. Moreover, as is clear to the skilled reader, said step S5 of optimizing the deformation predicted by the approximated biomechanical model, which comprises in this embodiment the optimization of the alignment between the deformed pre-operative data and the intra-operative data, typically comprises several iterations until the optimized, predicted deformation vector is determined. As is typical in and known for optimization procedures, an iterative process is used to get, iteration by iteration, closer to the finally determined optimization result, i.e., which in the present case is the optimized, predicted deformation vector. This iterative process is also reflected in the particular embodiments shown in FIGS. 3 and 6.

According to an embodiment of the presented method, the method comprises deforming intra-operative data with the determined deformation vector. This less intuitive embodiment, in which the intra-operative data are deformed and then compared with the pre-operative data, is another way of determining how good both match with each other. While this is mathematically not as exact as the approach mentioned before (i.e., deforming the pre-operative data and comparing them subsequently with the intra-operative data), this approach might be less complex. In a further embodiment, a cost function is then used for comparing the deformed intra-operative data with pre-operative data.

According to an embodiment of the presented method, also the approximated biomechanical model is a parametrized, patient-specific biomechanical model and is configured to predict a deformation of the at least one part of a patient body in the form of a deformation vector as an output.

In other words, the "approximation", i.e., the step S3 of calculating an approximated biomechanical model based on the S resulting deformation vectors, does not change the character of the model, which is a parametrized, patient-specific biomechanical model.

According to an embodiment of the presented method, the method further comprises the step of building the computer simulatable biomechanical model based on or by using the pre-operative data, that were acquired.

As was mentioned already before, as part of the normal surgical procedure, pre-operative data, like e.g., planning data is acquired before surgery. This data may depict the pre-operative patient anatomy and may be provided in higher quality as compared to other data used, like e.g., intra-operative data. The pre-operative data may also comprise intervention-specific annotations. Moreover, also additional other data may be acquired and used for building the computer simulatable biomechanical model. As another non-limiting example, in the process of building the model information about the surgical plan, e.g., the intended approach to the surgical site, may be acquired and used, or the intraoperative gravity direction with respect to the patient brain measured may be used in building/generating the computer simulatable biomechanical model. Other kind of data may of course also be used.

According to an embodiment of the presented method, the biomechanical model is configured to receive as input values for P different parameters $p_1, \ldots, p_P$; wherein the biomechanical model is configured to output a deformation vector based on the received input values $p_1, \ldots, p_P$.

This characterization of the model holds true for both the original model provided in step S1, as well as for the approximated biomechanical model calculated in step S3. Further, this embodiment describes the functional, mathematical nature of the model, i.e., that it receives P different parameter values and outputs a respective deformation vector. Non-limiting examples of such different parameters P, that are of particular use in brain surgery calculations, will be mentioned hereinafter in other embodiments.

According to an embodiment of the presented method, the optimization carried out in step S5 optimizes said values of said P parameters, wherein P<S holds true.

In other words, the number of parameters P is smaller than the number S of forward simulations that are carried out and the correspondingly calculated S deformation vectors. The "original", i.e., non-approximated, biomechanical model has P parameters. Therefore, the approximation of the model, for example by using a multivariate interpolation thereof, also has P degrees of freedom. In other words, in this embodiment the parameters of the approximated biomechanical model/of the multivariate interpolation corresponds precisely to the parameters of the original model. In case of, for example, using a mode decomposition approximation the approximated biomechanical model has, in general, M>P degrees of freedom, wherein M are the so-called mode weights, as will be explained in more detail hereinafter. The optimization procedure optimizes the values of these P or M, respectively, degrees of freedom to obtain an optimized deformation vector. Both M<S and P<S do hold true.

According to an embodiment of the presented method, the P different parameters comprise at least one of a level of cerebrospinal fluid, an amount of mass effect, i.e., a tumour-induced tissue deformation, an amount of deformation after tumour resection, an amount of fluid drainage, and an amount of pressure applied by a surgeon on a brain surface with a medical device, for example, an ultrasound probe during acquisition of ultrasound images.

Each of these parameters can affect the deformation state of a patient's body. Hence, these parameters, i.e., the respectively provided values thereof, are used in this embodiment to predict the deformation of the at least one part of the patient body during the optimization carried out in step S5.

According to an embodiment of the presented method, the P different parameters $p_1, \ldots, p_P$ define a parameter space $R^P$; and the step S3 of calculating the approximated biomechanical model based on the S resulting deformation vectors is an approximation carried out in the parameter space $R^P$ defined by the P different parameters $p_1, \ldots, p_P$.

In this embodiment during the step S5 of optimizing the deformation predicted by the approximated biomechanical model said P different parameters $p_1, \ldots, p_P$ are optimized. This optimization can beneficially be used in e.g., a multivariate interpolation of the biomechanical model, as will be explained now in more detail.

According to an embodiment of the presented method, the S calculated deformation vectors are N-dimensional vectors of a deformation space $R^N$ with N deformation degrees of freedom, wherein the step S3 of calculating the approximated biomechanical model comprises the step of determining a multivariate interpolation function for the S resulting deformation vectors (S3a), wherein the multivariate interpolation function is a function from parameter space $R^P$ to deformation space $R^N$.

In numerical analysis, multivariate interpolation is interpolation on functions of more than one variable; when the variates are spatial coordinates, it is also known as spatial interpolation. The function to be interpolated is known at given points and the interpolation problem consists of yielding values at arbitrary points.

In this embodiment, the approximated biomechanical model is the multivariate interpolation function. Briefly put, the multivariate interpolation technique approximates the model by interpolating between "nearby" simulation results. This approximation has the primary purpose of replacing the (comparatively expensive) forward solutions considered during the described optimization process with a cheaper, approximate computation. Following is a more precise mathematical description of this approach. The simulation model can be considered a function f from parameter space ($R^P$) to deformation space ($R^N$). Given values for the P parameters, it computes values for the N deformation degrees of freedom. Given S samples of this function within the relevant part of the parameter space, a multivariate interpolation function f⁻ that approximates f can be constructed and then employed in the optimization procedure. The technique is described using radial basis function (RBF) interpolation for illustration. As is clear to the skilled reader, also other interpolation method can be used according to other embodiments of the present invention.

Thus, according to an embodiment, the step S3a of determining the multivariate interpolation function comprises the step of carrying out a radial basis function (RBF) interpolation (S3b).

According to an embodiment, the step of carrying out the radial basis function (RBF) interpolation comprises the step of determining an S×N weight matrix W, wherein the determined weight matrix W comprises information derived from the S deformation vectors resulting from the S forward simulations of the biomechanical model carried out in step S2.

While the mathematical details of how to best set up such an RBF interpolation should be of lesser relevance to the presented embodiment, a brief overview is given. First, S so-called "test points" $p_1$ to $p_S$ in parameter space can be chosen, which is equivalent to choosing S sets of parameter values. And f is evaluated for these, i.e., corresponding forward simulations are carried out. After choosing an appropriate radial basis function $\varphi$, the following equation system is solved for the S×N weight matrix W:

$$\Phi W = F$$

$$\text{where } \Phi = \begin{bmatrix} \phi(\|p_1 - p_1\|) & \cdots & \phi(\|p_M - p_1\|) \\ \vdots & \ddots & \vdots \\ \phi(\|p_1 - p_S\|) & \cdots & \phi(\|p_S - p_S\|) \end{bmatrix}$$

$$W = \begin{bmatrix} w_{11} & \cdots & w_{1N} \\ \vdots & \ddots & \vdots \\ w_{S1} & \cdots & w_{SN} \end{bmatrix}$$

$$F = \begin{bmatrix} f(p_1)^T \\ \vdots \\ f(p_S)^T \end{bmatrix}$$

Then, for any point p in parameter space, an approximation of f is obtained by evaluating the following matrix-vector product:

$$f(p) \approx \tilde{f}(p) = W^T \begin{bmatrix} \phi(\|p_1 - p\|) \\ \vdots \\ \phi(\|p_S - p\|) \end{bmatrix}$$

One option for the choice of test points is to uniformly sample the parameter space in a grid, but also other choices of test points are of course usable. However, for efficient and beneficial use of computational resources, the test points should be distributed in the parameter space such that regions of greater interest (e.g., parameter combinations with higher prior likelihood of occurring in a real-world surgical setting) are sampled more densely.

To describe what the weight matrix entries mean, one could say the weight in row s and column n describes the influence of the radial basis function centered on $p_s$ (i.e., a point in parameter space) on the $n^{th}$ entry of the resulting deformation vector.

According to an embodiment, the step S3b of carrying out the radial basis function interpolation (RBF) comprises choosing a radial basis function, e.g. a Gaussian basis function, and optionally choosing a shape parameter, choosing S sets of P parameter values as center points of the radial basis function in parameter space, carrying out the S>1 forward simulations of step S2, and calculating the radial basis function (RBF) weights thereby determining the weight matrix W.

According to another embodiment of the computer implemented method, the step S3 of calculating an approximated biomechanical model comprises the step of carrying out a deformation mode decomposition of the calculated S deformation vectors, which were calculated in step S2, thereby determining M principal deformation modes of the S deformation vectors and/or M principal frequency modes of the S deformation vectors (step S3c).

In this embodiment, a second group of techniques is used, i.e., deformation mode decomposition. In this embodiment, principal modes are identified in the S deformations that were computed via forward simulations before. The biomechanical model can then be approximated by a linear combination of these principal modes. As is clear to the skilled reader, this embodiment is not limited to any particular choice of mode decomposition technique. In the following, the so-called Principal Component Analysis (PCA) of the simulated deformations will be described in more detail for illustration, but other techniques, like for example a Fourier decomposition, can of course also be used in principle to realize the teaching and benefits of this embodiment.

According to an embodiment, the computer implemented method, comprises the step of approximating the biomechanical model by a linear combination of the M determined principal deformation modes using M respective mode weights for each principal deformation mode, and/or approximating the biomechanical model by a linear combination of the M principal frequency modes using M respective mode weights for each principal frequency mode (step S3$d$).

As is clear to the skilled reader, this linear combination of the determined principal deformation modes/the linear combination of the M principal frequency modes is then the approximated biomechanical model used in the method presented herein. Said principal deformation modes may be identified by applying a PCA and the said principal frequency modes may be identified by applying a Fourier decomposition/Fourier analysis.

According to an embodiment, during the step S5 of optimizing the deformation predicted by the approximated biomechanical model said M mode weights are optimized.

In this embodiment the M mode weights are the parameters that are optimized during the optimization process defined in step S5. In other words, in this embodiment values for the M mode weights are searched that best align the observed pre- and intra-operative states of the patient. For example, a cost function can be used for comparing deformed pre-operative data with newly acquired intra-operative data. This cost function, for example image similarity or landmark distances, or the like, can then be optimized by an optimization algorithm. For a given choice of values of the M mode weights, a simulation is performed, i.e., the approximated biomechanical model is used to predict the deformation based on the chosen values of the M mode weights thereby multiplying each of the M deformation modes with the respective M mode weights and then summing them up, to obtain a corresponding deformation (i.e., deformation vector), the cost function can then be evaluated for this deformation, and the cost value can be reported to the optimization algorithm used. The optimization algorithm then either proceeds to select a new set of M mode weight values, or, after several iterations, asserts convergence.

According to an embodiment, the biomechanical model is configured to receive as an input values for P different parameters $p_1, \ldots, p_P$; and wherein the biomechanical model is configured to output a deformation vector based on the received input values $p_1, \ldots, p_P$; and M>P and M<S both hold true.

Note that the "original", i.e., the non-approximated biomechanical model has P parameters. The mode decomposition approximation has, in general, M>P degrees of freedom, i.e., the mode weights. The optimization procedure optimizes the values of these M degrees of freedom to obtain an optimized deformation vector. Both M<S and M>P do hold true.

Mathematically speaking, mode decomposition attempts to approximate the generally non-linear function f(p) through a linear combination of deformation modes:

$$f(p) \approx \tilde{f}(w(p)) = Uw$$

where U is an N×M matrix of deformation modes and w the M-dimensional vector of corresponding weights. Essentially, the inventors of the present invention have embedded the non-linear function f(p), which maps from parameter space $R^P$ into deformation space $R^N$, into the M-dimensional "mode space" $R^M$. The key property obtained is that f⁻(w) is linear in the M weight values w. This approximation generally has more degrees of freedom than the original model (M>P), necessitated by reproducing non-linear behavior through linear mode contributions. FIG. 8 illustrates this idea in an example where P=1 and M=2. In particular, FIG. 8 shows three forward simulations, and the two principal PCA modes (conceptually). The dashed outline corresponds to undeformed configuration. In this example, a 2D finite element model for some beam-like object suspended above a solid surface is considered. Of the six nodes, four (solid black) are unconstrained and two (empty circles) are fixed in place. The single parameter $p_1$ of the model is the strength of gravity g that the beam is subjected to (g=$p_1$). For low gravity values, the beam is elongated downward in a straightforward manner. However, beyond a certain gravity value, the beam makes contact with the solid surface and is additionally "squished", leading to outward movement of the lower nodes. This behavior is nonlinear, but can be (for the purpose of this example) captured by two independent deformation modes: Pure elongation (mode 1), and pure "squishing" (mode 2), as visualized in the lower part of the figure. Combining these deformation modes in various amounts allows reproducing the various deformation states, as illustrated in FIG. 9. FIG. 9 depicts the function f(p) represented/approximated by linear combination of modes. The function w(p) represents f(p) in mode space. For zero gravity, no deformation occurs (mode weights are zero). Up until the point of contact, only the elongation mode gains weight. For even higher gravity, both start increasing. The function w(p) describes exactly this, and forms a (1D) curve in the (2D) mode space. This example also illustrates the consequence of having more degrees of freedom in mode space than in the original model (M>P): "Unphysical" behavior (that is, behavior that the original model could not produce) becomes representable. This happens if one "departs" from w(p) and chooses mode weights that do not correspond to any parameter choice p of the model. Consider point D in FIG. 10, which does not lie on w(p). It thus does not correspond to a deformation the model would predict, although a "similar" simulation model with a higher surface position (shown with a dashed line in FIG. 10) theoretically could. In FIG. 10 point D in mode space does not correspond to a deformation the original model could predict.

In essence, this embodiment of the presented method trades plausibility guarantees for linearity of the simulation model approximation. To mitigate the effects of deviating from the predictions of the simulation model, regularization can optionally be used. One regularization approach involves penalizing high mode weights, whereby greater penalties may be applied to modes of lesser significance. The cost function itself might also effectively provide inherent regularization.

For example, using an image-based similarity as cost function will generally penalize nonphysical deformations, as they would lead to misalignments in at least parts of the image domain. Optionally, one could also establish (or approximate) the non-linear function w(p) itself. An optimization result $w_o$ could then be projected and/or compared to the closest "plausible" model configuration $p_o$ along w(p). A measure of distance from $w_o$ to $w(p_o)$ could also be interpreted and provided to the user as a measure of "plausibility" of the computed result. In the example, point D in FIG. 10 has low plausibility because of its distance to w(p).

According to an embodiment of the presented method, during the step of carrying out the deformation mode decomposition of the S deformation vectors a Principal Component Analysis (PCA) of the S deformation vectors is applied thereby identifying said M principal deformation modes of the S deformation vectors. Alternatively, or in combination therewith, a Fourier decomposition of the S deformation vectors is applied thereby identifying said M principal deformation modes of the S deformation vectors.

As mentioned, different techniques may be employed to arrive at a suitable U. Using a Singular Value Decomposition (SVD), which corresponds to performing a PCA, is described in more detail herein in the context of detailed, non-limiting embodiments. Other choices like a Fourier decomposition may also be used but are not detailed here. To establish U via the SVD, one may first compute S forward solutions for S choices of model parameters (see RBF explanation above). These N-dimensional solution vectors are again arranged in an N×S matrix F:

$$F^T = \begin{bmatrix} f(p_1)^T \\ \vdots \\ f(p_S)^T \end{bmatrix}$$

A reduced SVD of this rectangular matrix is computed:

$$F = U\Sigma V^T$$

yielding the N×M mode matrix U (each column corresponding to one deformation mode), as well as the corresponding singular values $\sigma_i$ in the diagonal of the diagonal matrix $\Sigma$. The singular values may be taken as a measure of relevance for the corresponding mode. One can thus choose M by, for example, only considering columns of U to be principal modes if their corresponding singular values are above a certain threshold. Both M=S and M<S are therefore possible.

In general, no matter the mode decomposition technique and mode importance criterion used, discarding modes of lesser importance may be beneficial: The size and degrees of freedom are reduced at minor or negligible cost to the approximation quality, which benefits the speed of the subsequent optimization.

According to an embodiment of the presented method, the S calculated deformation vectors are N-dimensional vectors of a deformation space $R^N$ with N deformation degrees of freedom, wherein in the step of carrying out the deformation mode decomposition of the S deformation vectors (step S3c) N deformation modes are calculated, the method further comprising the step selecting a subset of M deformation modes considered as the principal deformation modes (step S3d), and wherein M<N holds true and wherein M<S holds true.

While this embodiment related to the selection of the "main or principal" modes, the following embodiment relates to the assessment of the relevance of a singular main or principal mode. According to this embodiment, the selection of the subset of M deformation modes is based on a measure of mode relevance. In one embodiment, the measure of mode relevance is a relative magnitude of the corresponding singular value.

Note that the term "relative magnitude of the corresponding singular value", is to be understood as follows. As part of the singular value decomposition, one obtains a so-called "singular value" for each mode (~equivalent of an eigenvalue). Removing a mode with a large singular value incurs greater approximation error than removing a mode with a small singular value. When applying SVD, or, equivalently, PCA as explained hereinbefore in detail, one thus usually keeps either the M modes with the largest singular values, i.e., choosing M beforehand, or one decides that only modes with singular values above some threshold x are kept. To simplify the choice of x, one can normalize the singular values by dividing all of them by e.g., the largest singular value, which is then referred to herein as "relative magnitude". Hence, here the largest singular value always has relative magnitude 1.0.

In another embodiment, in case of a Fourier decomposition of the S deformation vectors, modes above a pre-defined threshold frequency are ignored. And in yet another embodiment, in case of a Fourier decomposition of the S deformation vectors, modes below a pre-defined threshold amplitude are ignored. As is clear to the skilled reader, these embodiments can of course be combined with the embodiment using the relative magnitude as mode relevance.

In an embodiment, the P different parameters used as input of the biomechanical model comprise at least one of a level of cerebrospinal fluid, an amount of mass effect, i.e., a tumour-induced tissue deformation and/or an amount of deformation after tumour resection, an amount of fluid drainage, and an amount of pressure applied by a surgeon on a brain surface with an ultrasound probe during acquisition of ultrasound images.

This was mentioned before and of course these exemplary parameters also apply for the deformation mode decomposition based method embodiment detailed hereinbefore.

According to an embodiment, the method further comprises the step of determining a score for a physical plausibility of the approximated biomechanical model based on a comparison of a projection from a point in mode space to parameter space.

To avoid physically implausible approximation results, this embodiment suggests determining the physical plausibility of the approximation and to use a comparison of the projection from the point in mode space to parameter space.

According to an embodiment of the presented method, the method further comprises the steps determining a respective range for each mode based on projecting each of the S initially computed deformation vectors into mode space thereby obtaining S sets of mode weights, and for each mode weight, setting an allowed range based on a minimum value and a maximum value of the S weight values of that mode thus obtained, and constraining each mode weight to a range between the minimum and the maximum value obtained for said mode.

To avoid physically implausible approximation results, this embodiment teaches that each mode weight can be constrained to an appropriate range, i.e., it must remain between a pre-defined minimum and a pre-defined maximum value specific to that mode. This range can be determined by projecting each of the S initially computed deformation vectors into mode space thus obtaining S sets of mode weights, and then, for each mode weight, setting the allowed range to span the minimum and maximum of the S weight values of that mode thus obtained.

Note that "constraining" shall be understood in this context as follows. In case a mode weight is outside of said range defined by the minimum and maximum value, it will be automatically set by the presented method to the closest extreme value, i.e., to the minimum in case the minimum is closer as the maximum value to actual value, or alternatively, it will be set to the maximum value should this value be closer. In this way, physically implausible approximation results are avoided, or at least minimized.

Note that M and S are not identical in this embodiment. There are M modes and M associated or respective mode weights. For each of the S "initially computed deformation vectors" M weights are calculated, respectively. Thus, M*S weights are calculated in total here. For each of the M mode weights one determines the minimum and maximum amongst the S associated weights, and based on this sets said "respective range for each mode", defining the upper and lower limit in this constraining process. Therefore, for weight m this results in:

$$\min_m = \min(\text{weight}_{m1}, \text{weight}_{m2}, \ldots, \text{weight}_{mS})$$

$$\max_m = \max(\text{weight}_{m1}, \text{weight}_{m2}, \ldots, \text{weight}_{mS})$$

wherein $\text{weight}_{1s}$ to $\text{weight}_{Ms}$ are the M mode weights for the "initially computed deformation vector" number s. In other words, one just projects all "initially computed deformation vectors" into mode space and then places a simple boundary or box around all these points in mode space, i.e., min and max in each of the M dimensions. If one goes beyond this boundary, one leaves the area of scenarios, which one had calculated with the biomechanical model, which most likely would result in less relevant or even useless deformations. Thus, this embodiment increases the accuracy of the predicted deformations.

In a particular embodiment, the step S5 of optimizing the deformation predicted by the approximated biomechanical model comprises simulating a deformation vector with the approximated biomechanical model based on e.g., several input parameter values of the different parameters (step S5a);

applying the simulated deformation vector to the acquired pre-operative data resulting in deformed pre-operative data (step S5b);

calculating a measure of agreement, i.e., a match, between the deformed pre-operative data and intra-operative patient data (step S5c), and optimizing a cost function (step S5d), which optimizes said measure of agreement between the deformed pre-operative data and the intra-operative patient data, by repeating said steps S5a, S5b and S5c, thereby determining the optimized, predicted deformation vector.

Thus, in this exemplary embodiment the optimized, predicted deformation vector is calculated by the computer implemented method in several iterations of said optimization. This will be elucidated in more detail in particular embodiments explained hereinafter. A particular advantage of this embodiment over the prior art is that the kind of cost function can be freely selected, no a priori restrictions for such a cost function exist when using the presented computer implemented method. Exemplary embodiments of cost functions are mentioned hereinafter.

According to another exemplary embodiment, the recording of intra-operative data triggers and/or causes an update of the previously mentioned method, and/or triggers/causes that the previously mentioned method is carried out.

According to an embodiment, the cost function uses at least one of an Euclidian distance for landmark pairs; average surface distance for point clouds/point surfaces; an image similarity measure, for example a local cross correlation, between the intra-operative patient data and the deformed pre-operative patient data; or any combination thereof.

Moreover, in a particular embodiment thereof, the cost function uses an Euclidian distance for landmark pairs, wherein each landmark pair comprises one landmark in the pre-operative data and one landmark in the intra-operative data, and the cost function measures a distance between these two landmarks after the deformation vector has been applied, i.e., after e.g., the landmark in the pre-operative data, has been deformed.

In other words, in this embodiment, each landmark pair comprises one landmark in the pre-operative data and one landmark in the intra-operative data acquired and used in this embodiment. In this embodiment, the cost function measures the geometrical distance between these two landmarks after the deformation vector has been applied (that is, after the e.g., preoperative landmark has been deformed). If a deformation vector moves the landmarks closer together, the cost function for that deformation vector decreases.

According to an embodiment, the cost function is mathematically differentiable with respect to the deformation vector, and the method further comprises the steps of mathematically differentiating the cost function with respect to the deformation vector thereby determining gradient information, and using said determined gradient information in the optimization carried out in steps S5.

Note that the use of gradient information serves to strongly reduce the number of optimization steps required. Enabling the resulting speedup is a key benefit of this embodiment of the present invention. For example, multivariate interpolation, as described herein in detail, provides a means of rapidly computing an approximation of the deformation for any given set of model parameters. Moreover, mode decomposition, as also described herein in detail, instead parametrizes the deformation space directly in a linear fashion. Both approaches can significantly speed up the derivative-free optimization procedure described above by replacing forward simulations with cheap-to-compute approximations. But importantly, in both cases the computation of the deformations to evaluate is now also differentiable with respect to the parameter values. If it possible to also establish the gradient of the cost function (that is, its partial derivatives with respect to the N deformation degrees of freedom), it can be backpropagated to the parameter values or mode weights, respectively. Then, a derivative-aware optimization procedure, e.g., nonlinear conjugate gradient, can be employed for rapid convergence towards the optimal parameter choice/mode weights, providing an even greater speedup. Most kinds of cost functions, like e.g., Euclidian distance for landmark pairs, average surface distance for point clouds/surfaces, local cross correlation for image similarity, or even combinations of these, admit the computation of a gradient along with the scalar cost value, making this embodiment very broadly applicable.

According to an embodiment, the method comprises the step of augmenting the approximated biomechanical model with additional translational degrees of freedom involving adding three additional parameters or weights, which each control global translation of the deformation vector in one particular axis direction.

A practical challenge in the application of the presented method lies in the pre-alignment of the pre- and intra-operative data. Ideally, both data should be brought into the same frame of reference in order to compute the cost function, i.e., the quality of alignment between intra-operative and deformed pre-operative data. This may be accomplished by establishing a rigid transformation, i.e., translation+rotation, between the data reference frames. The accuracy of this rigid transformation can substantially influence the cost function and thus the predictions the method eventually arrives at. A significant benefit of the presented method lies in the potential to compensate for such inaccuracies caused, for example, by finite accuracy of optical tracking methods with little additional effort. For example, for both RBF interpolation and mode decomposition, as detailed hereinbefore and hereinafter, it is possible to augment the model approximation with additional translational degrees of freedom. This involves adding three additional parameters/weights, which each control global translation of the deformation field in one particular axis direction. This augmentation does not correspond to predicted mechanical deformations of the patient tissues themselves, but to a predicted error in the data pre-alignment, which is thereby accounted for. Importantly, the earlier described backpropagation of cost function gradient information onto the parameters works also for these augmented degrees of freedom. Thus, these embodiments can of course be combined. Their optimal values can thus be found together with all the remaining parameters/weights in a time-efficient manner. This ability to optionally compensate for imperfect alignment input data is very valuable in the practical application of the described method and thus a key benefit of this embodiment.

According to an embodiment, the method comprises the step of displaying the deformed pre-operative data to a user.

In the end, the practitioner/user would like the computed deformation to closely match the pre-operative data to some observed intra-operative state of the patient. The presented method matches this need and with displaying the finally deformed pre-operative data, i.e., using the finally determined and optimal deformation vector, is a fast and accurate method of providing the user with correct and up-to-date, i.e., current data.

According to another embodiment, the method comprises the step of triggering a pre-calculation of the computer simulatable biomechanical model, wherein this triggering is caused when a gravity vector is recorded and/or when a gravity vector is provided/accessible.

According to another embodiment, the intra-operative data as mentioned herein comprise optionally/additionally at least one of 2D X-ray data, landmarks, which were extracted and/or segmented from image data.

In a second aspect, the invention is directed to a program which, when running on a computer or when loaded onto a computer, causes the computer to perform the method steps of the method aspect and embodiments disclosed herein.

The program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a program storage medium on which a program is stored, which, when running on a computer or when loaded onto a computer, causes the computer to perform the method steps of the method aspect and embodiments disclosed herein. The program storage medium preferably is a non-transitory computer-readable program storage medium on which the program is stored.

In a fourth aspect, the invention is directed to a medical system, comprising the program of the second aspect or the program storage medium of the third aspect.

In other words, this medical system is configured to carry out the methods described herein. In particular, this medical system is configured to:

acquire, or alternatively build, a computer simulatable biomechanical model of the at least one part of a patient body;

wherein the biomechanical model is a parametrized, patient-specific biomechanical model for predicting the deformation of the at least one part of the patient body, the method further comprising the steps;

wherein the medical system is further configured for carrying out S>1 forward simulations of the biomechanical model thereby calculating S resulting deformation vectors;

calculating an approximated biomechanical model based on the S resulting deformation vectors;

acquiring pre-operative data;

optimizing, in a calculative manner, a deformation predicted by the approximated biomechanical model, which results in an optimized, predicted deformation vector; and deforming the pre-operative data by applying the optimized, predicted deformation vector to the pre-operative patient data.

In a further embodiment, the medical system comprises at least one electronic data storage device storing the computer simulatable biomechanical model; and at least one communication interface configured for acquiring intra-operative patient data.

For example, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to the calculation of data by a processor and/or computer. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data/image data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data"/"acquiring an image" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
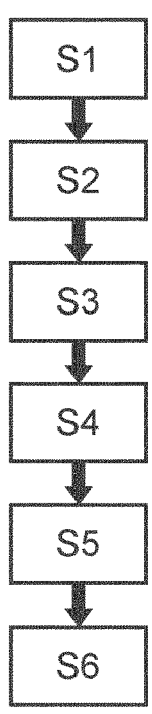
FIG. 1 illustrates a flow diagram of the computer-implemented method of predicting a deformation of at least one part of a patient body according to the first aspect of the present invention.

FIG. 1 illustrates a flow diagram of the computer-implemented method of predicting a deformation of a part of a patient body with steps S1 to S6. The presented method can be applied for several different medical scenarios, one of which is neurosurgical scenario, where the prediction of intra-operative deformations primarily relates to "brain shift", i.e., the deformation of the patient brain during and due to the surgical intervention. During surgery, patient bodies/patient tissues generally undergo deformations, which may lead to a mismatch between pre-operative planning data and reality. The purpose of the presented computer implemented method shown in FIG. 1 is to facilitate a correction of such deformations, which is achieved by calculating said optimized, predicted deformation vector by means of said steps S1 to S5 detailed hereinbefore and hereinafter. As is clear to the skilled reader, when deforming the pre-operative data in step S5 by applying said optimized, predicted deformation vector to the pre-operative patient data, said correction is realized. The method thus comprises the following steps:

providing a computer simulatable biomechanical model of the at least one part of a patient body (step S1);

wherein the biomechanical model is a parametrized, patient-specific biomechanical model for predicting the deformation of the at least one part of the patient body, the method further comprising the steps carrying out S>1 forward simulations of the biomechanical model thereby calculating S resulting deformation vectors (step S2);

calculating an approximated biomechanical model based on the S resulting deformation vectors (step S3);

acquiring pre-operative data (step S4);

optimizing, in a calculative manner, a deformation predicted by the approximated biomechanical model, which results in an optimized, predicted deformation vector (step S5); and deforming the pre-operative data by applying the optimized, predicted deformation vector to the pre-operative patient data (step S6).

The inventors of the present invention have found that in this way the deformed pre-operative data can be provided in a comparatively short amount of time, while a high accuracy of the prediction of the deformation can still be ensured. The purpose of the approximation of the model in step S3 is speeding up the optimization procedure, but not by having fewer degrees of freedom than the original model. Rather, the approximation once established is much simpler and faster to compute. As was set out hereinbefore, in a particular embodiment the approximation is differentiable, which again substantially benefits the speed of the optimization procedure.

The calculation method shown in FIG. 1 can beneficially make use of the time before a surgical intervention takes place and can carry out steps S1, S2 and S3 before such an intervention. Thus, the provision of the computer simulatable biomechanical model (step S1), the S>1 forward simulations of the biomechanical model together with the calculation of the S resulting deformation vectors (step S2), as well as the calculation of the approximated biomechanical model based on the S resulting deformation vectors (step S3) can beneficially be carried out before such an intervention, which can save valuable calculation time when running calculations on a computer during an intervention. In that sense, the presented computer-implemented method of FIG. 1 allows for a highly efficient pre-calculation of the approximated biomechanical model. This will be elucidated even more with the following embodiments of FIGS. 2 to 10. Moreover, in some embodiments the step S5 of optimizing the deformation predicted by the approximated biomechanical model comprises several iterations until the optimized, predicted deformation vector is determined. As is typical in optimization procedures, an iterative process may be used to get, iteration by iteration, closer to optimized, predicted deformation vector determined in step S5. This iterative aspect will be explained in more detail in the context of the embodiments of FIG. 3 and FIG. 5, for example.

Figure 2:
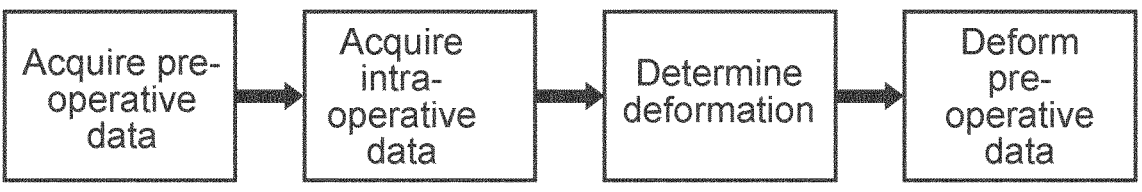
FIG. 2 illustrates a flow diagram of correction methods that are used in embodiments of the present invention.

FIG. 2 illustrates a flow diagram of correction methods that can be used in embodiments of the present invention. As mentioned before, during surgery, patient bodies/patient tissues generally undergo deformations, which may lead to a mismatch between pre-operative (e.g., planning) data and reality. The purpose of the presented computer implemented method is to facilitate a correction of such deformations. The principal procedure for doing so is shown in FIG. 2. As part of the normal surgical procedure, pre-operative data, like e.g., planning data is acquired before surgery. This data typically depicts the pre-operative patient anatomy, usually in high quality and with intervention-specific annotations (e.g., outlined tumor and/or edema, fiber tracts, landmarks). Further data may be acquired specifically to inform an optionally comprised simulation model construction/generation. For example, information about the surgical plan, e.g., the intended approach to the surgical site, may be incorporated, or the intraoperative gravity direction with respect to the patient brain measured. During the optimization of the calculated predicted deformation, i.e., step S5 shown in FIG. 1, an observation of the current patient state during the intervention can be used. Thus, intra-operative data can be acquired in particular embodiments, for example by CT, MRI or US imaging, or by acquisition of point or surface data. This data may be sparse, e.g., few slices/points, partial, e.g., the field of view covers only part of the surgical site, or of low or lower fidelity, e.g., low resolution, low accuracy, as compared to typical pre-operative data. The reduced quality of this intra-operative data is generally due to a trade-off between acquisition quality and acquisition speed, as time is an important constraint during surgical interventions.

Figure 3:
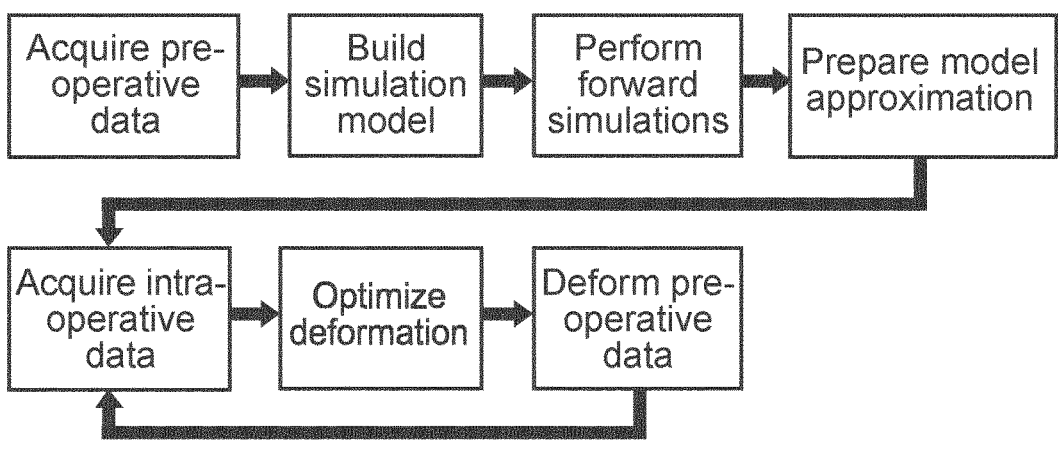
FIGS. 3 to 7 each illustrate a flow diagram of a particular embodiment of the method of the present invention.

Next, a more detailed description is given of the steps involved in a particular method embodiment shown in FIG. 3. Pre-operative data is acquired as described above. Some or all of this data is then used to construct a simulation model of the relevant organs and tissues of the patient, for example the brain tissue, in case of a cranial intervention. The fundamental purpose of the simulation model is to predict deformations of the preoperative patient state ("forward solution"). That is, the result computed by running such a ("forward") simulation is a physically plausible deformation of the patient anatomy from the pre-operative state (i.e., pre-operative data) to some intra-operative state. In the end, one would like the computed deformation to closely match the pre-operative data to some observed intra-operative state of the patient. In the presented method shown in FIG. 3, the simulation model is "explored" in an initial phase by performing several forward simulations, followed by preparing an approximation of the model. Crucially, this phase may happen before intra-operative data is acquired, and can thus be done before an alignment between pre-operative data and intra-operative data is requested by the user and calculated by the computer/processor. This in turn allows a suitably chosen optimization procedure to rapidly compute the desired deformation. The pre-operative data can thus be deformed to match the current patient state with minimal time expenditure after acquisition of intra-operative data.

This deformation can also be used as a starting point for computation of further updates, should new intra-operative data become available.

Regarding the simulation model and the forward simulations used the following should be noted. The computer-implemented method of predicting a deformation of a patient body shown in FIG. 3 makes no assumptions about the mathematical, biological or physical underpinnings of the simulation model, or the means by which a solution is computed, which differs from the prior art. For example, the following properties could be influenced by/during the course of surgery: the amount of mass effect reversal due to tumor resection, in cranial cases, the amount of cerebrospinal fluid drained from the skull, the amount of pressure applied by a surgical tool, changes in tissue properties (e.g. stiffness, compressibility) due to e.g. medication. The simulation model used in FIG. 3 can incorporate these effects and control their "strength" with corresponding parameters. Thus, deformations can be predicted for different surgical scenarios by performing simulations with different choices for the parameter values. One approach is therefore to search values for the parameters that best align the observed pre- and intra-operative states of the patient—an inverse problem. In the embodiment of FIG. 3, a cost function is established for comparing deformed pre-operative data with newly acquired intra-operative data. This cost function (for example image similarity or landmark distances as mentioned before) is then optimized by an optimization algorithm: For a given choice of parameter values, perform a simulation to obtain a corresponding deformation, evaluate the cost function for this deformation, and report the cost value to the optimization algorithm. The optimization algorithm then either proceeds to select a new set of parameter values, or, after several iterations, asserts convergence.

Figure 4:
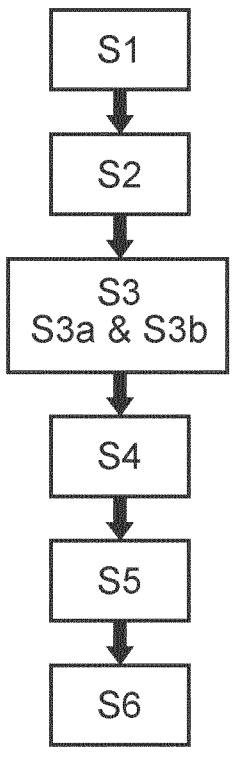

FIG. 4 illustrates another embodiment of the computer-implemented method of predicting a deformation of a part of a patient body using radial basis function (RBF) interpolation. The method of FIG. 4 is based on the method described before for FIG. 1, and additionally comprises the method steps S3a and S3b. Moreover, in this method the biomechanical model is configured to receive as an input values for P different parameters $p_1, \ldots, p_P$; and the biomechanical model is configured to output a deformation vector based on the received input values $p_1, \ldots, p_P$. The S calculated deformation vectors are N-dimensional vectors of a deformation space $R^N$ with N deformation degrees of freedom. The step S3, i.e., calculating an approximated biomechanical model based on the S resulting deformation vectors, comprises the step of determining a multivariate interpolation function for the S resulting deformation vectors (step S3a), wherein the multivariate interpolation function is a function from parameter space $R^P$ to deformation space $R^N$. Moreover, the step S3a of determining the multivariate interpolation function comprises the step of carrying out a radial basis function (RBF) interpolation (step S3b). Briefly put, this embodiment approximates the biomechanical model by interpolating between "nearby" simulation results. This approximation has the primary purpose of replacing the (comparatively expensive) forward solutions considered during the described optimization process with a cheaper, approximate computation. The simulation model can be considered a function f from parameter space (RP) to deformation space (RN). Given values for the P parameters, it computes values for the N deformation degrees of freedom. Given S samples of this function within the relevant part of the parameter space, a multivariate interpolation function f~ that approximates f can be constructed and then employed in the optimization procedure. More details and embodiments of the radial basis function (RBF) interpolation have been described hereinbefore.

Figure 5:
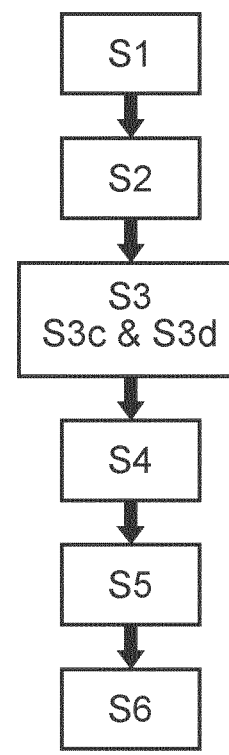

FIG. 5 illustrates another embodiment of the computer-implemented method of predicting a deformation of a part of a patient body using mode decomposition. The method of FIG. 5 is based on the method described before for FIG. 1, and additionally comprises the method steps S3c and S3d. In the embodiment of FIG. 5 the step S3 of calculating an approximated biomechanical model comprises the step of carrying out a deformation mode decomposition of the calculated S deformation vectors, which were calculated in step S2, thereby determining M principal deformation modes of the S deformation vectors and/or M principal frequency modes of the S deformation vectors (step S3c). Moreover, the method of FIG. 3 further comprises the step of approximating the biomechanical model by a linear combination of the M determined principal deformation modes using M respective mode weights for each principal deformation mode, and/or approximating the biomechanical model by a linear combination of the M principal frequency modes using M respective mode weights for each principal frequency mode (step S3d). Thus, principal modes are identified in the S deformations that were computed via forward simulations in step S2. The model is then approximated by a linear combination of these principal modes. For example, Principal Component Analysis of the simulated deformations can be used, but other techniques like e.g. Fourier decomposition can also be used in principle. Mathematically speaking, mode decomposition attempts to approximate the generally non-linear function f(p) through a linear combination of deformation modes:

$$f(p) \approx \tilde{f}(w(p)) = Uw$$

where U is an N×M matrix of deformation modes and w the M-dimensional vector of corresponding weights. Essentially, we have embedded the (non-linear) function f(p), which maps from parameter space $R^P$ into deformation space $R^N$, into the M-dimensional "mode space" $R^M$. The key property obtained is that f~(w) is linear in the M weight values w. This approximation generally has more degrees of freedom than the original model (M>P), necessitated by reproducing non-linear behaviour through linear mode contributions. This non-linear behaviour is elucidated also in the context of FIGS. 8 to 10, which were discussed in detail hereinbefore.

Figure 6:
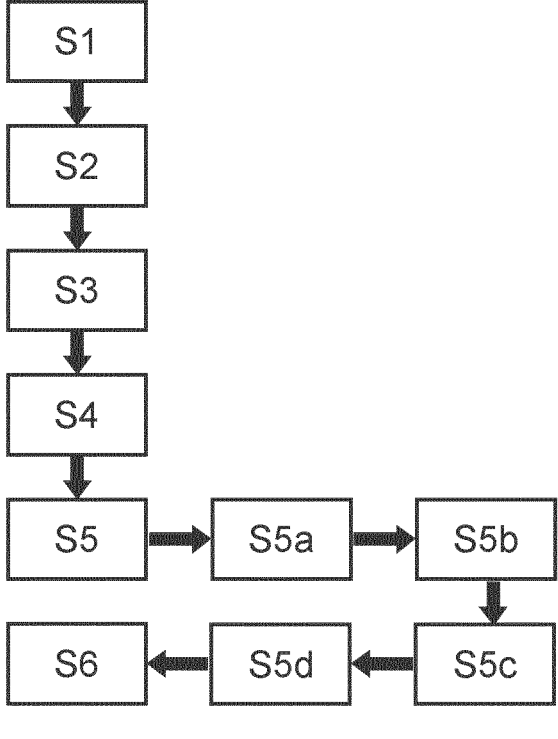

FIG. 6 illustrates another embodiment of the computer-implemented method of predicting a deformation of a part of a patient body, which elucidates several iterations during the optimization step S5. The method of FIG. 6 is based on the method described before for FIG. 1, and additionally comprises the method steps S5a to S5d. In the embodiment of FIG. 6 the step S5 of optimizing the deformation predicted by the approximated biomechanical model comprises the steps:

using the approximated biomechanical model for simulating a deformation vector based on P input parameter values of the P different parameters $p_1, \ldots, p_P$ (step S5a);

applying the simulated deformation vector to the acquired pre-operative data resulting in deformed pre-operative data (step S5b);

calculating a measure of agreement between the deformed pre-operative data and intra-operative patient data (step S5c), and optimizing a cost function (step S5d), which optimizes said measure of agreement between the deformed pre-operative data and the intra-operative patient data, by repeating steps S5a, S5b and S5c, thereby determining the optimized, predicted deformation vector. In other words, the used cost function, for example image similarity or landmark distances as explained in detail hereinbefore, can then be optimized by an optimization algorithm. For a given choice of parameter values, a simulation is performed to obtain a corresponding deformation, evaluate the cost function for this deformation, and report the cost value to the optimization algorithm.

The optimization algorithm then either proceeds to select a new set of parameter values, or, after several iterations, asserts convergence. As is clear to the skilled reader, said step S5 of optimizing the deformation predicted by the approximated biomechanical model, typically comprises several iterations until the optimized, predicted deformation vector is determined. As is typical in and known for optimization procedures, an iterative process is used to get, iteration by iteration, closer to the finally determined optimization result, i.e., which in the present case is the optimized, predicted deformation vector finally determined.

Figure 7:
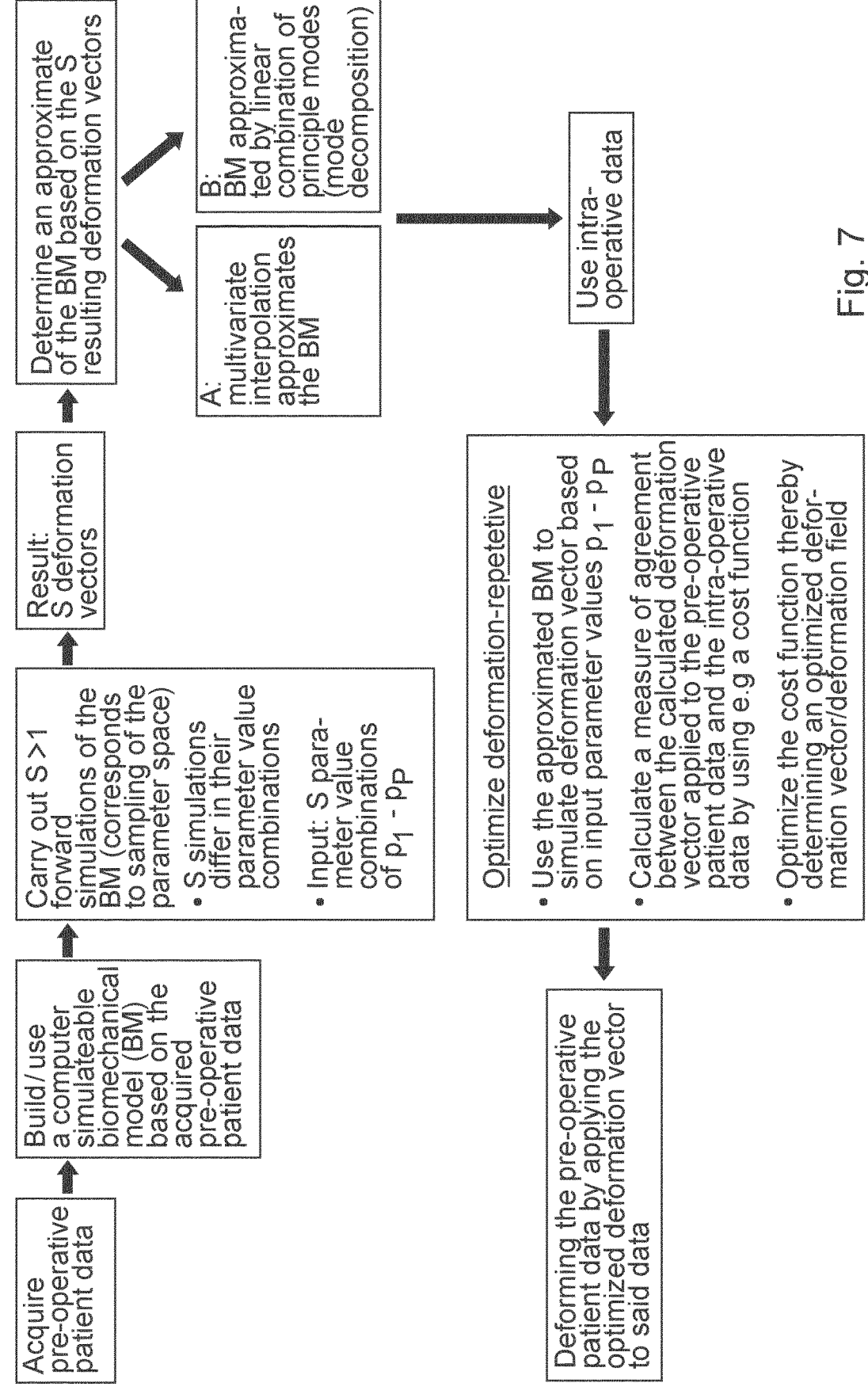
Figure 8:
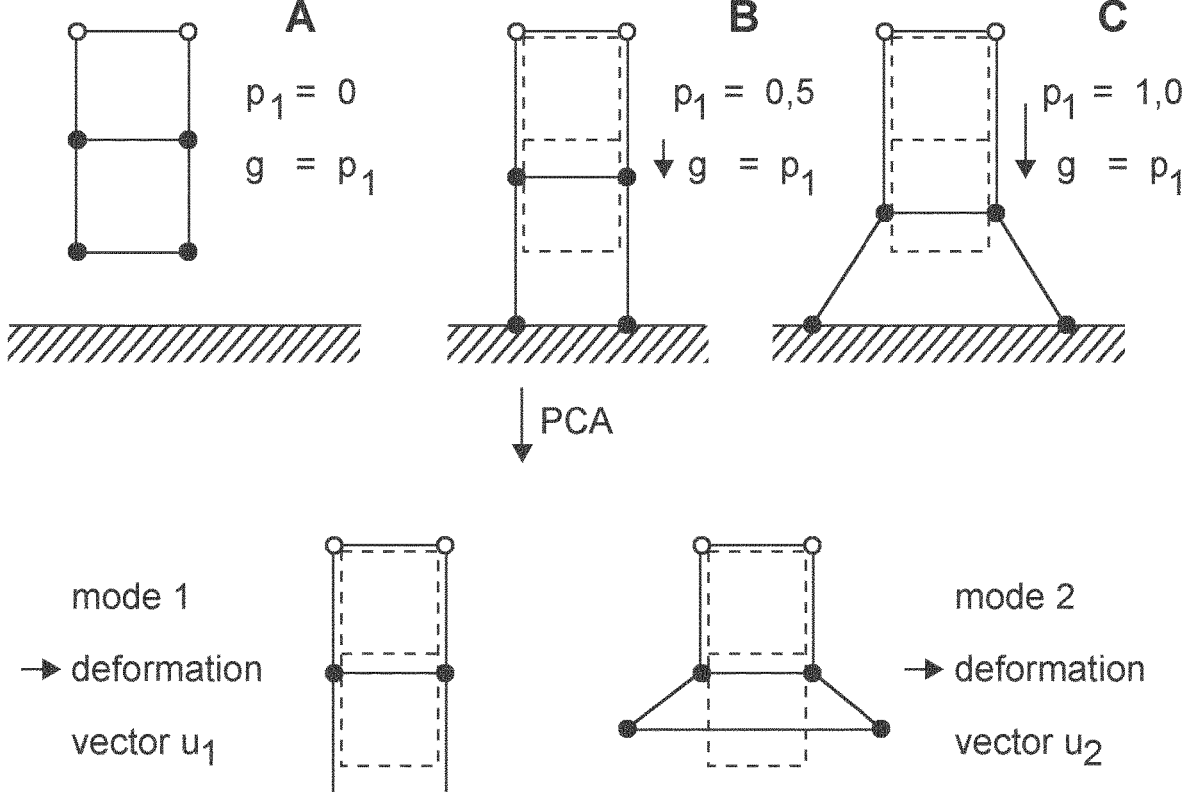
FIG. 8 schematically shows three forward simulations, and the two principal PCA modes used in an embodiment of the present invention.
Figures 9, 10:
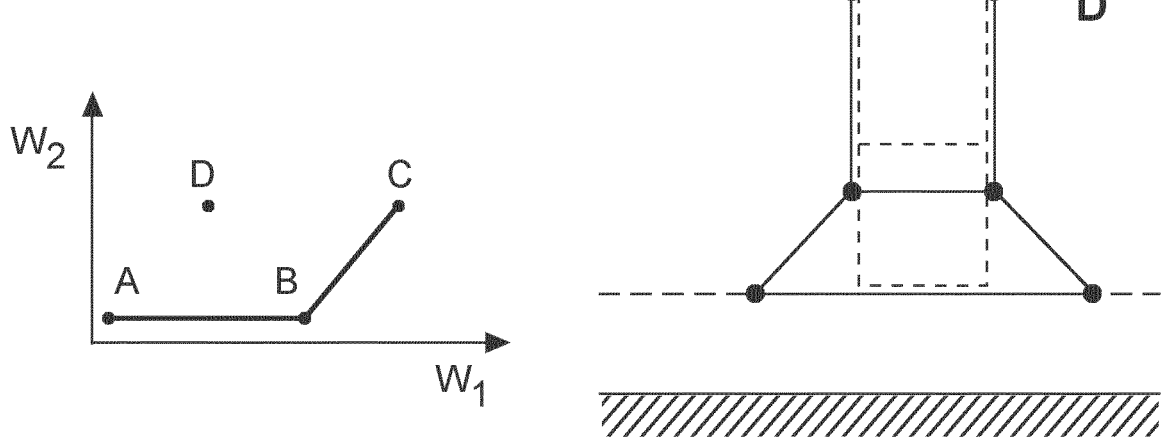
FIG. 9 schematically shows the function f(p) represented/approximated by linear combination of modes as used in an embodiment of the present invention.
FIG. 10 schematically shows that point D in mode space does not correspond to a deformation the original model could predict.

FIG. 7 shows another particular embodiment of the computer-implemented method of predicting a deformation of a part of a patient body. In a first step, pre-operative patient data are acquired, and they are used in a second step to build a computer simulateable biomechanical model (BM). Next, S>1 forward simulations of the BM are carried out, which corresponds to sampling of the parameter space. This results in S deformation vectors. As a next step, an approximation of the BM is determined based on the S resulting deformation vectors. In a first embodiment A, a multivariate interpolation approximates the BM, and in an alternative embodiment B the BM is approximated by linear combination of principal modes using mode decomposition. Moreover, intra-operative data are used in the following optimization procedure. In a repetitive way, the deformation is optimized. In detail, the approximated BM is used to simulate deformation vectors based on input parameter values $p_1$-$p_P$. Then, a measure of agreement is calculated between the calculated deformation vector applied to the pre-operative patient data and the intra-operative data by using e.g. a cost function. The cost function is then optimized thereby determining an optimized deformation vector/deformation field. Finally, the pre-operative patient data is deformed by applying the optimized deformation vector to said data.

The invention claimed is:

1. Computer-implemented method of predicting a deformation of at least one part of a patient body, the method comprising:

providing a computer simulatable biomechanical model of the at least one part of a patient body wherein the biomechanical model is a parametrized, patient-specific biomechanical model for predicting the deformation of the at least one part of the patient body, the method further comprising:

carrying out S>1 forward simulations of the biomechanical model thereby calculating S resulting deformation vectors;

calculating by at least one processor, an approximated biomechanical model based on the S resulting deformation vectors;

acquiring pre-operative data;

optimizing, by at least one processor, a deformation predicted by the approximated biomechanical model, which results in an optimized, predicted deformation vector; and deforming, by at least one processor, the pre-operative data by applying the optimized, predicted deformation vector to the pre-operative patient data.

2. The computer-implemented method according to claim 1, wherein the approximated biomechanical model is a parametrized, patient-specific biomechanical model and is configured to predict a deformation of the at least one part of a patient body in the form of a deformation vector as an output.

3. The computer-implemented method according to claim 1, the method further comprising the step: building the computer simulatable biomechanical model based on the acquired pre-operative data.

4. The computer-implemented method according to claim 1, wherein the biomechanical model is configured to receive as an input values for P different parameters $p_1, \ldots, p_p$; and wherein the biomechanical model is configured to output a deformation vector based on the received input values $p_1, \ldots, p_p$.

5. The computer-implemented method according to claim 4, wherein the optimization optimizes the values of said P parameters, and wherein the number P parameters is less than number S forward simulations.

6. The computer-implemented method according to claim 4, wherein the P different parameters comprise at least one of a level of cerebrospinal fluid, an amount of a tumour-induced tissue deformation and/or an amount of deformation after tumour resection, an amount of fluid drainage, and an amount of pressure applied by a surgeon on a brain surface with an ultrasound probe during acquisition of ultrasound images.

7. The computer-implemented method according to claim 4, wherein the P different parameters $p_1, \ldots, p_p$ define a parameter space Rp; and wherein the step S3 of calculating the approximated biomechanical model based on the S resulting deformation vectors is an approximation carried out in the parameter space $R^P$ defined by the P different parameters $p_1, \ldots, p_p$.

8. The computer-implemented method according to claim 4, wherein the S calculated deformation vectors are N-dimensional vectors of a deformation space $R^N$ with N deformation degrees of freedom, wherein the step of calculating the approximated biomechanical model comprises the step of determining a multivariate interpolation function for the S resulting deformation vectors, and wherein the multivariate interpolation function is a function from parameter space $R^P$ to deformation space $R^N$.

9. The computer-implemented method according to claim 8, wherein the step of determining the multivariate interpolation function comprises the step of carrying out a radial basis function interpolation.

10. The computer-implemented method according to claim 9, wherein carrying out the radial basis function interpolation comprises the step of determining an S×N weight matrix W, and wherein the determined weight matrix W comprises information derived from the S deformation vectors resulting from the S forward simulations of the biomechanical model.

11. The computer-implemented method according to claim 9, wherein the step of carrying out the radial basis function interpolation comprises choosing a radial basis function and optionally choosing a shape parameter, choosing S sets of P parameter values as center points of the radial basis function in parameter space, carrying out the S>1 forward simulations, and calculating the radial basis function weights thereby determining the weight matrix W.

12. The computer-implemented method according to any of the claim 1, wherein the step of calculating an approximated biomechanical model comprises the step carrying out a deformation mode decomposition of the calculated S deformation vectors, which were calculated in step, thereby determining M principal deformation modes of the S deformation vectors and/or M principal frequency modes of the S deformation vectors.

13. The computer-implemented method according to claim 12, the method further comprising:

approximating the biomechanical model by a linear combination of the M determined principal deformation modes using M respective mode weights for each principal deformation mode, and/or approximating the biomechanical model by a linear combination of the M principal frequency modes using M respective mode weights for each principal frequency mode.

14. The computer-implemented method according to claim 13, wherein during the step of optimizing the deformation predicted by the approximated biomechanical model said M mode weights are optimized.

15. The computer-implemented method according to claim 14, wherein the biomechanical model is configured to receive as an input values for P different parameters $p_1, \ldots, p_P$; and wherein the biomechanical model is configured to output a deformation vector based on the received input values $p_1, \ldots, p_P$; and wherein M>P and M<S hold true.

16. The computer-implemented method according to claim 15, wherein the P different parameters comprise at least one of a level of cerebrospinal fluid, an amount of mass effect, i.e., a tumour-induced tissue deformation and/or an amount of deformation after tumour resection, an amount of fluid drainage, and an amount of pressure applied by a surgeon on a brain surface with an ultrasound probe during acquisition of ultrasound images.

17. The computer-implemented method according to claim 13, the method further comprising:

determining a probability value representing a physical plausibility of the approximated biomechanical model based on a comparison of a projection from a point in mode space to parameter space.

18. The computer-implemented method according to claim 13, the method further comprising:

determining a respective range for each mode based on projecting each of the S initially computed deformation vectors into mode space thereby obtaining S sets of mode weights, and for each mode weight, setting an allowed range based on a minimum value and a maximum value of the S weight values of that mode thus obtained, and constraining each mode weight to a range between the minimum and the maximum value obtained for said mode.

19. The computer-implemented method according to claim 13 wherein during the step of carrying out the deformation mode decomposition of the S deformation vectors a Principal Component Analysis of the S deformation vectors is applied thereby identifying said M principal deformation modes of the S deformation vectors; and/or wherein during the step of carrying out the deformation mode decomposition of the S deformation vectors a Fourier decomposition of the S deformation vectors is applied thereby identifying said M principal deformation modes of the S deformation vectors.

20. The computer-implemented method according to claim 12, wherein the S calculated deformation vectors are N-dimensional vectors of a deformation space $R^N$ with N deformation degrees of freedom, wherein in the step of carrying out the deformation mode decomposition of the S deformation vectors N deformation modes are calculated, the method further comprising the step selecting a subset of M deformation modes considered as the principal deformation modes, and wherein M<N holds true and wherein M<S holds true.

21. The computer-implemented method according to claim 20, wherein the selection of the subset of M deformation modes is based on a measure of mode relevance.

22. The computer-implemented method according to claim 21, wherein the measure of mode relevance is a relative magnitude of a corresponding singular value; or in case of a Fourier decomposition of the S deformation vectors modes above a pre-defined threshold frequency are ignored; and/or in case of a Fourier decomposition of the S deformation vectors modes below a pre-defined threshold amplitude are ignored.

23. The computer-implemented method according to claim 1, wherein the step of optimizing the deformation predicted by the approximated biomechanical model further comprises:

using the approximated biomechanical model for simulating a deformation vector based on P input parameter values of the P different parameters $p_1 \ldots, p_P$;

applying the simulated deformation vector to the acquired pre-operative data resulting in deformed pre-operative data;

calculating a measure of agreement between the deformed pre-operative data and intra-operative patient data, and optimizing a cost function, which optimizes said measure of agreement between the deformed pre-operative data and the intra-operative patient data, by repeating the optimizing steps, thereby determining the optimized, predicted deformation vector.

24. The computer-implemented method according to claim 23, wherein the cost function uses at least one of an Euclidian distance for landmark pairs; average surface distance for point clouds/point surfaces; an image similarity measure, between the intra-operative patient data and the deformed pre-operative patient data; or any combination thereof.

25. The computer-implemented method according to claim 24, wherein the cost function uses an Euclidian distance for landmark pairs, wherein each landmark pair comprises one landmark in the pre-operative data and one landmark in the intra-operative data, and wherein the cost function measures a distance between these two landmarks after the deformation vector has been applied, i.e., after e.g., the landmark in the pre-operative data, has been deformed.

26. The computer-implemented method according to claim 23, wherein the cost function is mathematically differentiable with respect to the deformation vector, and the method further comprising the steps mathematically differentiating the cost function with respect to the deformation vector thereby determining gradient information, and using said determined gradient information in the optimizing steps.

27. The computer-implemented method according to claim 1, further comprising:

augmenting the approximated biomechanical model with additional translational degrees of freedom involving adding three additional parameters or weights, which each control global translation of the deformation vector in one particular axis direction.

28. The computer-implemented method according to claim 1, the method further comprising:

displaying the deformed pre-operative data to a user.

29. A non-transitory computer readable medium comprising instructions which when executed by at least once processor, cause at least one processor to:

provide a biomechanical model of at least one part of a patient body, wherein the biomechanical model is a parametrized, patient-specific biomechanical model for predicting a deformation of the at least one part of the patient body, the method further comprising:

carry out S>1 forward simulations of the biomechanical model thereby calculating S resulting deformation vectors;

calculate by at least one processor, an approximated biomechanical model based on the S resulting deformation vectors;

acquire pre-operative data;

optimize, by at least one processor, a deformation predicted by the approximated biomechanical model, which results in an optimized, predicted deformation vector; and deform, by at least one processor, the pre-operative data by applying the optimized, predicted deformation vector to the pre-operative patient data.

30. A medical system comprising:

at least one computer having at least one processor operable to:

provide a biomechanical model of at least one part of a patient body, wherein the biomechanical model is a parametrized, patient-specific biomechanical model for predicting a deformation of the at least one part of the patient body, the method further comprising:

carry out S>1 forward simulations of the biomechanical model thereby calculating S resulting deformation vectors;

calculate by at least one processor, an approximated biomechanical model based on the S resulting deformation vectors;

acquire pre-operative data;

optimize, by at least one processor, a deformation predicted by the approximated biomechanical model, which results in an optimized, predicted deformation vector; and deform, by at least one processor, the pre-operative data by applying the optimized, predicted deformation vector to the pre-operative patient data at least one electronic data storage device storing the computer simulatable biomechanical model; and at least one communication interface configured for acquiring intra-operative patient data.

* * * * *